United States Patent [19]

Kawamura et al.

[11] Patent Number: 4,521,406

[45] Date of Patent: Jun. 4, 1985

[54] ANTITUMOR AGENT

[75] Inventors: Yasuo Kawamura, Kyoto; Tadashi Nishiyama, Kadoma; Tomiyoshi Itoh, Suita; Takuo Sakai, Sakai, all of Japan

[73] Assignee: Chisso Corporation, Osaka, Japan

[21] Appl. No.: 265,563

[22] Filed: May 20, 1981

[30] Foreign Application Priority Data

May 22, 1980 [JP] Japan ................................. 55-68300

[51] Int. Cl.³ ..................... A61K 37/48; A61K 31/70; A61K 31/505
[52] U.S. Cl. ....................................... 424/94; 514/274
[58] Field of Search ......................... 424/94, 251, 180

[56] References Cited

PUBLICATIONS

Chemical Abstracts 91:69278t (1979).

Primary Examiner—Jerome D. Goldberg
Attorney, Agent, or Firm—Wenderoth, Lind & Ponack

[57] ABSTRACT

An antitumor agent comprising a combination of 5-fluorocytosine and cytosinedeaminase has been developed. As to the practical administration procedure of the agent, it is preferable to carry out in such a manner that 5-fluorocytosine is first administered in any portion of the body, and cytosinedeaminase is then administered into the topically suffered portion. The administered 5-fluorocytosine is transferred into the suffered portion, and the 5-fluorocytosine is affected with the action of cytosinedeaminase to convert the former compound into 5-fluorouracil, resulting in that the necrosis of the tumor tissue is caused.

5 Claims, No Drawings

ANTITUMOR AGENT

BACKGROUND OF THE INVENTION

This invention relates to a novel anti-malignant tumor agent comprising a combination of 5-fluorocytosine and cytosinedeaminase. It is understood that the term "tumor" as employed herein means tumors sensitive to 5-fluorouracil.

Nowadays, a considerably large number of compounds are used as antitumor agents for clinical treatment. They include, for example, alkylating agents, nucleic acid-type antimetabolites, antitumor antibiotics, and hormonal agents, and the like. In many cases, however, these antitumor agents are used against leukemia and malignant lymphoma and the like, and few are effective against solid tumors such as stomach cancer, and the like. Although 5-fluorouracil is known to be effective against solid tumors, it has the drawback of intense toxicity in oral and intravenous administrations.

There was suggested tetrahydrofuryl 5-fluorouracil as an orally administrable agent free from this drawback. This compound in fact has low toxicity, however, its antitumor activity is also low, accordingly.

In an attempt to remove these drawbacks of known antitumor agents, the present inventors have made an effort to develop new therapeutic agents against malignant tumors which have lower toxicity and higher efficacy. These investigations have led to the unexpected discovery that administration, preferably topical administration, of cytosinedeaminase in the presence of 5-fluorocytosine causes necrosis of tumor tissues alone without giving any adverse effect on the entire human body.

SUMMARY OF THE INVENTION

It is an object of this invention to provide an antitumor agent comprising a novel combination of known compounds.

The present invention provides an antitumor agent comprising a combination of 5-fluorocytosine and cytosinedeaminase.

DETAILED DESCRIPTION OF THE INVENTION

The 5-fluorocytosine used in the invention is one of the derivatives synthesized during the development of 5-fluorouracil. While 5-fluorouracil shows intense antitumor activity, 5-fluorocytosine shows no antitumor activity. When administered into a human body, 5-fluorocytosine is not at all metabolized because no transferase therefor exists in the human body, resulting in that a greater part of the compound is excreted out of the body in a form of 5-fluorocytosine per se and thus does not adversely affect the human body. In 1963, Grundenberg discovered that the 5-fluorocytosine has antimycotic activity, and it is now practically used as an excellent antifungal agent.

Cytosinedeaminase, in the other hand, acts on the amino group of a cytosine to induce de-amination, thereby converting the cytosine to a uracil. Cytosinedeaminase having such converting action is present in microorganisms such as fungi, *Escherichia coli*, and microorganisms of the genera Pseudomonas and Serratia and the like, but is not existent in the human body. The cytosinedeaminase per se has no antitumor activity.

As mentioned above, although individually neither 5-fluorocytosine nor cytosinedeaminase has antitumor activity, the combined use of these compounds develops an antitumor effect. This effect of the antitumor agent of the invention is demonstrated by the following Experimental Examples 1 to 4 (in vitro tests) and Experimental Examples 5 and 6 (in vivo tests).

EXPERIMENTAL EXAMPLE 1

HeLa cells were inoculated in a concentration of $1 \times 10^5$ cells/ml in an Eagle MEM medium containing 10% of FCS, and then an aliquot of 4 ml of the suspension was poured into each of Falcon plastic flasks, followed by stationary cultivation for 24 hours by a cultivating vessel at 37° C. in an atmosphere of $CO_2$. After confirming that mono-layer culture was formed, the culture was contacted for 24 hours with an agent consisting of 5-fluorocytosine and cytosinedeaminase. Then, the culture was washed with PBS to remove the agent, and again cultivated for additional 4 days. After the cultivation, the living cells were counted by a leukocytometer, the ratio of killed cells was calculated.

The following were conducted as controls:
(a) the contacting with the agent was not performed; and
(b) 5-fluorocytosine and cytosinedeaminase were individually used to contact and treat the culture with the agent under the same conditions for 24 hours.

The results are shown in Table 1.

TABLE 1

| | Effects for growth inhibition in the treatment of HeLa cells | | | | | | | |
|---|---|---|---|---|---|---|---|---|
| | Control | | | Invention (5-fluorocytosine and cytosinedeaminase) | | | | |
| | | | | Treating Conditions | | | | |
| Number of days elapsed | Non-treated | 5-fluoro-cytosine | cytosine-deaminase | 1 µg/ml | 5 µg/ml | 10 µg/ml | 25 µg/ml | 50 µg/ml |
| 0 | 29 | 29 | 29 | 29 | 29 | 29 | 29 | 29 |
| 1 | — | treated with drug | treated with drug | treated with drug | treated with drug | treated with drug | treated with drug | treated with drug |
| 2 | 73 | 73 | 73 | 57 | 55 | 55 | 52 | 49 |
| 4 | 123 | 120 | 121 | 76 | 52 | 48 | 43 | 39 |
| 6 | 202 | 205 | 200 | 115 | 54 | 41 | 30 | 26 |

Note 1:
The figures shown in Table 1 refer to the number of cells ($\times 10^{-4}$ cells/ml).
Note 2:
The dose of cytosinedeaminase was 0.1 IU per milligram of 5-fluorocytosine.

As is clear from the above table, when 5-fluorocytosine or cytosinedeaminase is used alone, growth of the cells is seen as in the case of not treating the culture.

Accordingly, this shows that 5-fluorocytosine and cytosinedeaminase when used singly do not have any antitumor activity. In contrast, in a group treated with the antitumor agent of the invention consisting of a combination of 5-fluorocytosine and cytosinedeaminase, a considerable inhibition of the increase of the number of cells was noted even when the concentration of the agent was 1 μg/ml. When the concentration is 10 to 50 μg/ml, no increase in the number of cells was noted, and the agent showed a marked inhibiting action.

With respect to the ratio to be used of cytosinedeaminase to 5-fluorocytosine, the cytosinedeaminase can be used in an amount ranging from 0.01 to 1.0 IU per 1 mg of 5-fluorocytosine. Even if the cytosinedeaminase is used in an excessive amount more than 1.0 IU, an antitumor effect does not increase accordingly. It is preferable to use the cytosinedeaminase in an amount ranging from 0.05 to 0.5 IU.

EXPERIMENTAL EXAMPLE 2

Using four kinds of human cerebral tumor cells cultivated through one generation, the cell killing effect of the antitumor agent of the invention was examined in the same way as in Experimental Example 1. The results are shown in Table 2.

TABLE 2

| Concentration of the agent (μg/ml) | Ratio (%) of killed cells in the treatment of human cerebral tumor cells | | | |
| --- | --- | --- | --- | --- |
| | Cerebral tumor cells | | | |
| | Glioblastoma | Meningioma | Neurinoma | Astrocytoma |
| 10 | 46 | 43 | 30 | 26 |
| 25 | 60 | 54 | 44 | 44 |
| 50 | 73 | 57 | 54 | 51 |
| 100 | 89 | 68 | 63 | 57 |

Note:
The antitumor agent consisted of 5-fluorocytosine and cytosinedeaminase. 0.1 IU of cytosinedeaminase was used per milligram of 5-fluorocytosine.

The results in Table 2 demonstrate that when the combination of 5-fluorocytosine and cytosinedeaminase in accordance with this invention was used, the ratio of killed cells was 26 to 46% at a concentration of 10 μg/ml, and 51 to 73% at a concentration of 50 μg/ml.

EXPERIMENTAL EXAMPLE 3

A suspension of HeLa cells in a concentration of $1 \times 10^5$ cells/ml was poured in an amount of 4 ml into each of Falcon plastic flasks, and cultivated for 48 hours in a cultivation vessel at 37° C. in an atmosphere of $CO_2$. After confirming that mono-layer culture was formed, thymidine in a concentration of $1 \times 10^{-3}$ M was contacted twice with the culture to perform S-stage synchronization. After removal of the thymidine, the synchronized cells were contacted for 6 hours with a combination of 5-fluorocytosine and cytosinedeaminase 6 hours later ($G_2M$-stage) and 12 hours later ($G_1$-stage). The number of cells immediatelly after contact with the antitumor agent and that 96 hours later was calculated, and the cell growth inhibition ratio was determined. The results are shown in Table 3.

TABLE 3

| Cell growth inhibition ratio (%) in the respective stages of synthronization | |
| --- | --- |
| Cell cycle | Inhibition ratio (%) |
| S stage | 76.7 |
| $G_2M$ stage | 55.2 |
| $G_1$ stage | 49.5 |

It is seen from the above table that the contact treatment with the antitumor agent in the S stage showed a higher inhibition ratio than in the $G_1$ and $G_2M$ stages.

EXPERIMENTAL EXAMPLE 4

When human Glioblastoma was treated with 5-fluorocytosine in a concentration of 50 μg/ml, morphological changes such as the disintegration of the cytoplasm and the deformation of the nucleus were evidently noted.

EXPERIMENTAL EXAMPLE 5

The agent of the present invention was tested in vivo.
A tumor fragment of carcinoma 755 was aseptically cut to small pieces, and transplanted into the subcutaneous site of the back of mice by means of a transplating needle. Starting at 24 hours after the transplantation, 5-fluorocytosine was administered intraperitoneally and cytosinedeaminase, into the tumor tissues, both once a day for 9 consecutive days. On the tenth day, the tumor was enucleated, and its weight was measured. The tumor growth ratio (%) against the weight of tumor in a control group was calculated. The results are shown in Table 4.

5-Fluorocytosine can be used in an amount ranging from 1 to 100 mg/kg/day.

TABLE 4

| Tumor growth ratio (%) against control groups | |
| --- | --- |
| Drug | 5-fluorocytosine |
| 3 mg/kg/day | 69% |
| 5 mg/kg/day | 63% |

The results given in Table 4 show that reduction and necrosis of the tumor tissues occurred in the tumor to which 5-fluorocytosine and cytosinedeaminase had been administered.

As to the ratio to be used of cytosinedeaminase to 5-fluorocytosine, there can be used the cytosinedeaminase in an amount ranging from 0.03 to 1.0 IU per 1 mg of 5-fluorocytosine. Even though there is used the cytosinedeaminase in an excessive amount more than 1.0 IU, an antitumor effect does not increase, accordingly.

EXPERIMENTAL EXAMPLE 6

Glioblastoma cancer cells were transplanted in an amount of $2 \times 10^7$ into the brain of rats. Starting at 4th day after the transplantation, 4 ml of 5-fluorocytosine (concentration 10 mg/ml) was administered intraperitoneally once a day on every other day, and 0.02 ml of cytosinedeaminase (concentration 1 IU/ml) was administered to the site of transplantation of the cancer cells four times (4, 6, 8 and 10 days later). The number of days during which the experimental animals survived after transplantation of the cancer cells was determined.

To a control group I, nothing was administered after the transplantation.

To a control group II, 0.02 ml of PBS (concentration 1/15 mole) was administered instead of cytosinedeaminase under the same conditions as in the test group.

The average number of days of survival is shown in Table 5.

TABLE 5

|  | Drug administered | Number or rats | Average days of survival |
|---|---|---|---|
| Control group I | — | 10 | 33 days |
| Control group II | 5-fluorocytosine plus PBS | 10 | 32 days |
| Test group | 5-fluorocytosine plus cytosine-deaminase | 10 | 54 days |

It is thus seen that the combined use of 5-fluorocytosine and cytosinedeaminase showed a marked life-prolonging effect.

When administered to a human, the 5-fluorocytosine in accordance with this invention moves in a relatively high concentration to the tumor tissues. For example, when 5-fluorocytosine is administered to a patient with mycetogenic cephalomeningitis, the concentration of the 5-fluorocytosine in the cerebrospinal fluid is 120 μg/ml (1 to 2 hours after administration), and this concentration can be easily maintained. When cytosinedeaminase is topically administered to the tumor tissues to which 5-fluorocytosine has been previously administered, 5-fluorocytosine is converted to 5-fluorouracil within the tumor tissues without doing harm to a tumor bearing body and thus exhibits an antitumor effect. It is characteristically noted in this case that 5-fluorocytosine moves to the cerebral tumor tissues after passage through the cerebral barrier. Accordingly, the antitumor agent in accordance with this invention is very effective as a therapeutic agent for encephalophyma.

In actual treatment of encephalophyma, a special basket containing cytosinedeaminase may be embedded topically in a patient with encephalophyma in whom entire enucleation of the tumor seems impossible. In this case, cytosinedeaminase can be dissolved out continuously or intermittently. When 5-fluorocytosine is administered systemically, it moves to the cerebral tumor and under the action of cytosinedeaminase, changes to 5-fluorouracil which finally necroses the tumor tissues.

Investigations of the present inventors have also shown that although cytosinedeaminase is effective even when it is administered into the tumor at desired times, its effect can be caused to last for a longer period of time by including it in a cellulose pallet, etc., and this is clinically useful.

In the treatment of cancerous meningitis of the base for which no effective remedy has been available, 5-fluorocytosine may be systemically administered and cytosinedeaminase, into the cerebrospinal fluid cavity repeatedly, on the basis of the above theory. This leads to the possibility of diminishing the tumor tissues and improving the condition.

From the same standpoint, an improvement in condition can be expected on epipharynx cancer, which is difficult to cure and is even tragic, by administering 5-fluorocytosine and then perfusing or intermittently injecting a solution of cytosinedeaminase through the carotis externia which is a locally perfusable carotid.

The antitumor agent of this invention therefore is very valuable in practical applications.

What is claimed is:

1. An antitumor agent for use against solid tumors sensitive to 5-fluorousacil in humans comprising a combination of 5-fluorocytosine and cytosinedeaminase, said agent containing cytosindeaminase in an amount of 0.03 to 1.0 IU per milligram of 5-fluorocytosine whereby 5-fluorouracil is formed.

2. A method for treating a solid tumor sensitive to 5-fluorouracil in humans, which comprises contacting the tumor with a necrosis inducing amount of an antitumor agent comprising a combination of 5-fluorocytosine and cytosindeaminase, wherein cytosindeaminase is used in an amount of 0.03–1.0 IU per milligram of 5-fluorocytosine whereby 5-fluorouracil is formed.

3. A method for treating a solid tumor as in claim 2 which comprises first administering 5-fluorocytosine in any portion of a human body, followed by locally administering cytosinedeaminase to the area of the body where the solid tumor is present.

4. A method for treating a solid tumor as claimed in claim 3 wherein the 5-fluorocytosine is administered in an amount ranging from 1 to 100 mg/kg/day.

5. A method for treating a solid tumor as claimed in claim 4 wherein the cytosinedeaminase is administered in an amount ranging from 0.03 to 1.0 IU per 1 mg of the 5-fluorocytosine.

* * * * *